(12) United States Patent
Fütterer et al.

(10) Patent No.: US 10,100,974 B2
(45) Date of Patent: Oct. 16, 2018

(54) STAND WITH DEVICE FOR DISTORTION COMPENSATION

(71) Applicants: Franz Fütterer, Püchersreuth (DE); Harald Graf, Speichersdorf (DE); Stefan Hesl, Eschenbach (DE); Michael Kleber, Eslarn (DE); Jürgen Plannerer, Kemnath (DE); Stefan Popp, Waldershof (DE)

(72) Inventors: Franz Fütterer, Püchersreuth (DE); Harald Graf, Speichersdorf (DE); Stefan Hesl, Eschenbach (DE); Michael Kleber, Eslarn (DE); Jürgen Plannerer, Kemnath (DE); Stefan Popp, Waldershof (DE)

(73) Assignee: Siemens Aktiengesellschaft, München (DE)

( * ) Notice: Subject to any disclaimer, the term of this patent is extended or adjusted under 35 U.S.C. 154(b) by 111 days.

(21) Appl. No.: 14/496,982

(22) Filed: Sep. 25, 2014

(65) Prior Publication Data

US 2015/0085991 A1 Mar. 26, 2015

(30) Foreign Application Priority Data

Sep. 26, 2013 (DE) .......... 10 2013 219 415

(51) Int. Cl.
*A61B 6/00* (2006.01)
*F16M 13/02* (2006.01)
(Continued)

(52) U.S. Cl.
CPC ......... *F16M 13/022* (2013.01); *A61B 6/4464* (2013.01); *A61B 6/547* (2013.01);
(Continued)

(58) Field of Classification Search
CPC ... A61B 6/4405; A61B 6/4452; A61B 6/4464; A61B 6/4429; A61B 6/4435; A61B 6/44; A61B 6/4476
See application file for complete search history.

(56) References Cited

U.S. PATENT DOCUMENTS

| | | | |
|---|---|---|---|
| 5,818,638 A | 10/1998 | Nakamura | |
| 2005/0007553 A1* | 1/2005 | Romanoff | B66F 11/048 352/243 |

(Continued)

FOREIGN PATENT DOCUMENTS

| | | |
|---|---|---|
| CN | 101146973 A | 3/2008 |
| CN | 101243979 A | 8/2008 |

(Continued)

OTHER PUBLICATIONS

German Office Action dated May 16, 2014 in corresponding German Patent Application No. DE 10 2013 219 415.3 with English translation.

(Continued)

*Primary Examiner* — Hoon Song
(74) *Attorney, Agent, or Firm* — Lempia Summerfield Katz LLC

(57) ABSTRACT

An X-ray stand includes a device that compensates for distortions caused by weight. The stand includes a horizontal bracket. The device for distortion compensation includes an inclination-angle transmitter that generates an inclination signal as a function of an inclination angle of the bracket. The device also includes a control device that receives the inclination signal from the inclination-angle transmitter, a motor drive that is activated by the control device, and an adjustment device that is driven by the motor drive and is configured to adjust the inclination angle of the bracket. The control device activates the motor drive such that any (Continued)

deviation of the inclination angle of the bracket from a predefined inclination angle is reduced.

15 Claims, 3 Drawing Sheets

(51) Int. Cl.
    *F16M 11/10*     (2006.01)
    *F16M 11/18*     (2006.01)
    *F16M 11/20*     (2006.01)
    *F16M 11/28*     (2006.01)

(52) U.S. Cl.
    CPC ............. *F16M 11/10* (2013.01); *F16M 11/18* (2013.01); *F16M 11/2014* (2013.01); *F16M 11/2092* (2013.01); *F16M 11/28* (2013.01); *F16M 13/027* (2013.01); *F16M 11/2021* (2013.01)

(56) References Cited

U.S. PATENT DOCUMENTS

| | | |
|---|---|---|
| 2005/0253034 A1 | 11/2005 | Bally et al. |
| 2006/0226308 A1 | 10/2006 | White et al. |
| 2008/0192896 A1 | 8/2008 | Beimler et al. |
| 2010/0215152 A1* | 8/2010 | Takahashi ............ A61B 6/4429 378/197 |
| 2012/0175475 A1* | 7/2012 | McErlane .............. A47B 91/02 248/188.2 |
| 2013/0202093 A1 | 8/2013 | Meyer et al. |

FOREIGN PATENT DOCUMENTS

| | | |
|---|---|---|
| CN | 101621946 A | 1/2010 |
| DE | 19842436 A1 | 3/2000 |
| DE | 102009006764 A1 | 9/2010 |
| DE | 102012201857 A1 | 8/2013 |
| EP | 0994065 A1 | 4/2000 |
| KR | 100765633 B1 * | 10/2007 |

OTHER PUBLICATIONS

Chinese Office Action for Chinese Patent Application No. 201410493869.4, dated Aug. 18, 2016.

* cited by examiner

STAND WITH DEVICE FOR DISTORTION COMPENSATION

This application claims the benefit of DE 10 2013 219 415.3, filed on Sep. 26, 2013, which is hereby incorporated by reference in its entirety.

BACKGROUND

The present embodiments relate to a stand for medical imaging or engineering (e.g., an X-ray stand) including a device that compensates for distortions caused by weight.

Stands such as those used in medical imaging (e.g., X-ray stands) may have a vertical arm and a horizontal bracket that is supported on the vertical arm. The vertical arm may be a telescopic tube assembly having a length that may be varied in a vertical direction, for example. The functional component to be supported by the stand (e.g., an X-ray source or X-ray detector) is then supported on the horizontal bracket. The bracket may likewise be adjustable in length, and may also be rotatable about a vertical axis and a horizontal axis. The bracket is aligned as precisely as possible horizontally (e.g., level).

If a different orientation of the bracket is desired (e.g., an orientation that is other than precisely level but nonetheless has a horizontal orientation component), the same applies accordingly. The bracket is to be aligned as precisely as possible in the desired orientation in each case. For the sake of simplicity and irrespective of the alignment that is actually desired, reference is therefore made in the following to a horizontal bracket. Horizontal bracket denotes a bracket having an alignment that is precisely horizontal or a bracket having an alignment that has at least a horizontal orientation component.

The force due to weight of the functional component that is supported on the bracket, and the horizontal distance of the component from the vertical arm, produce a torque that is exerted on the vertical arm by the horizontal bracket. The magnitude of this torque depends on the distance in a horizontal direction of the functional component, which represents a lever. The magnitude of the torque also depends on the mass of the functional component.

The stand may be distorted by the force due to weight of the functional component and the torque that is generated thereby. As a result of the torque loading of the bracket, the extension of the tubular assembly follows a path that is no longer perfectly vertical, but is slightly inclined. Since the bracket is securely connected to the telescopic tube assembly, the bracket is tilted slightly out of the horizontal orientation. The horizontal bracket may be bent by the force due to weight of the functional component. The suspension or support of the component in the vertical arm may be deflected by the torque. The distortion ultimately results in unwanted deflection from the horizontal of the horizontal bracket and any functional component that is supported thereon.

The horizontal bracket is therefore to be returned to the desired horizontal orientation (e.g., nutation) by a suitable configuration (e.g., nutational adjustment). If the torque of the bracket changes (e.g., due to movement of the axes (vertical and horizontal adjustment, rotation) and corresponding masses and the consequently varying lever arms), the alignment is to be reset every time. In this case, the nutational adjustment is set via setting screws, discs, wedges or the like. In practice, frequent resetting is very resource-intensive and is often not possible at all. Therefore, in many cases, an average value is set, and the deviations are simply accepted.

The publication U.S. Pat. No. 5,818,638 A1 discloses a jib arm for supporting an optical apparatus. Unwanted deformation of the jib arm may occur due to the weight of the optical apparatus. In order to counteract such deformation, sensors are provided for the measurement thereof. The sensors are controlled by a kinematic system including multiple parts and multiple joints.

The publication DE 10 2012 201 857 A1 discloses a C-arm X-ray device including a mobile C-arm with multiple axes. Unwanted deformation of the C-arm may occur due to the dead weight and mechanical vibrations during certain movements. In order to be able to compensate for this deformation, optical sensors based on, for example, lasers are attached to both ends of the C-arm. The sensors allow precise measurement of current changes to the respective position. Based on the the position measurements, unwanted changes may be counteracted by correcting the C-arm.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an inexpensive device for distortion compensation of a stand including a horizontal bracket, where the device may compensate for deflection from the horizontal of the horizontal bracket and any functional component that is fixed thereto, is provided.

One embodiment of a stand includes a horizontal bracket and a device for distortion compensation. The device includes an inclination-angle transmitter that generates an inclination signal as a function of the inclination angle of the bracket, and a control device that receives the inclination signal from the inclination-angle transmitter. The device also includes a motor drive that is activated by the control device, and an adjustment device that is driven by the motor drive and is configured to adjust the inclination angle of the bracket. The control device activates the motor drive such that any deviation of the inclination angle of the bracket from a predefined inclination angle is reduced.

The orientation or inclination of the bracket is detected by a sensor, and regulation is effected accordingly for the purpose of equalization. The desired horizontal orientation may also be controlled using empirically determined equalization values according to the position of the bracket. The setting is effected by a motor-driven device in each case (e.g., via an eccentric, a screw-thread drive, a tapered disc or the like).

The nutational or small adjustment is therefore advantageously not set to a fixed value, but is adapted automatically depending on the loading of the bracket and the resulting distortion and/or the distortion of the tubular assembly. A sensor may detect the required values in this case. The bracket is therefore always supported in the desired horizontal orientation (e.g., level or inclined at a predefined inclination angle).

According to a development, the inclination-angle transmitter is an inclination-angle sensor. If the orientation or inclination of the bracket is detected by a sensor, regulation may be effected in order to equalize the deformation of the bracket, specifically by setting the desired horizontal orientation via motor-driven means as a function of the sensor signal. The setting is effected by a motor-driven device in each case (via an eccentric, a screw-thread drive, a tapered disc or the like).

According to a development, the stand includes an arm that is vertically length-adjustable and on which the horizontal bracket is supported. The inclination-angle transmitter receives a vertical position signal from the stand control device. The signal is correlated to the vertical length adjustment of the arm, and generates the inclination signal depending on the vertical position signal. The accuracy of the equalization control may be improved in this way, since the deformation also depends on the length of the vertical arm. Specifically, the longer the vertical arm, the greater deformation of the vertical arm is due to the torque exerted by the horizontal bracket.

According to another development, the stand includes a bracket that is horizontally length-adjustable, and the inclination-angle transmitter receives a horizontal position signal from a stand control device. The signal is correlated to the horizontal length position of the bracket, and generates the inclination signal depending also on the horizontal position signal. Based on the horizontal position of the bracket that is thus known, deformation compensation may be effected using previously and empirically determined equalization values, specifically by setting the desired horizontal orientation via a motor-driven device using a previously and empirically determined motor-driven equalization movement according to the horizontal position of the bracket. The setting is effected by a motor-driven device in each case (e.g., via an eccentric, a screw-thread drive, a tapered disc or the like).

According to a further development, an X-ray detector or X-ray source is supported on the horizontally length-adjustable bracket. A device for distortion compensation is thus realized for a conventional X-ray stand installation. Any distortion due to the weight of X-ray sources or X-ray detectors may thus be counteracted, thereby improving the image quality of the X-ray images. The weight of sources or detectors is in some cases considerable.

Although the foregoing explanations relate to a one-armed or two-armed stand, the present embodiments may also be used for distortion compensation in the case of stands having different numbers of stand arms and axes of motion, and having differently shaped stand arms.

DETAILED DESCRIPTION

Figure 1:
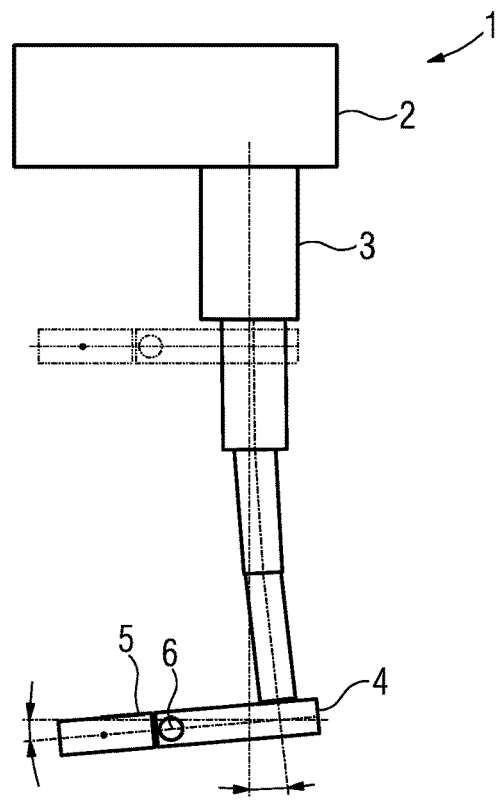
FIG. 1 shows one embodiment of a stand with deformation of a vertical arm.

FIG. 1 shows one embodiment of a stand 1 with deformation of a vertical arm 3. The stand 1 includes a top support 2 that houses components that are used for control and operation of the stand 1 but are not shown in FIG. 1. The stand 1 is connected to an X-ray device via lines that are likewise not shown.

The top support 2 holds a vertically length-adjustable arm 3 in the form of a telescopic tube assembly. The vertically length-adjustable arm 3 in the illustration is shown both extended (e.g., having significant vertical length) and retracted (e.g., marked by a dashed line).

A horizontal bracket 4 is supported on a lower end of the vertical arm 3. Via the vertical length adjustment of the arm 3, the height of the horizontal bracket 4 may be adjusted. The horizontal bracket 4 may also be rotated about the vertical arm 3. An X-ray source or X-ray detector 5 is movably supported on the horizontal bracket 4. The X-ray source or X-ray detector 5 is mounted via a pivot 6 so as to be rotatable relative to the horizontal bracket 4, representing a further degree of freedom for the movement of the X-ray source 5. The three possible movements allow flexible positioning of the X-ray source or X-ray detector 5.

The X-ray source or X-ray detector 5 is arranged so as to be horizontally separated from the vertical arm 3 by a distance that is predetermined by the horizontal bracket 4. This horizontal distance may also be variable if the horizontal bracket 4 is configured so as to be horizontally length-adjustable. The horizontal distance of the X-ray source or X-ray detector 5 from the vertical arm 3 acts as a lever, by which a force due to weight of the X-ray source or X-ray detector 5 exerts a toque on the vertical arm 3 or on the support of the horizontal bracket 4 in the vertical arm 3. This torque causes a deformation (e.g., of the vertical arm 3) that increases with the length of the vertical arm 3. This is shown schematically and exaggerated in FIG. 1. In FIG. 1, the deformation is significant when the length of the vertical arm is significant, but is small when the length of the vertical arm 3 is small (e.g., marked by a dashed line).

The deformation of the vertical arm 3 results in an inclination of the arm 3 relative to the vertical. This results in an inclination of the horizontal bracket 4 relative to the horizontal as indicated by two angle arrows in the illustration. This inclination produces inaccuracies in the positioning of the X-ray source or X-ray detector 5, which have a negative effect on the image quality of X-ray images taken by the X-ray source or X-ray detector 5.

Figure 2:
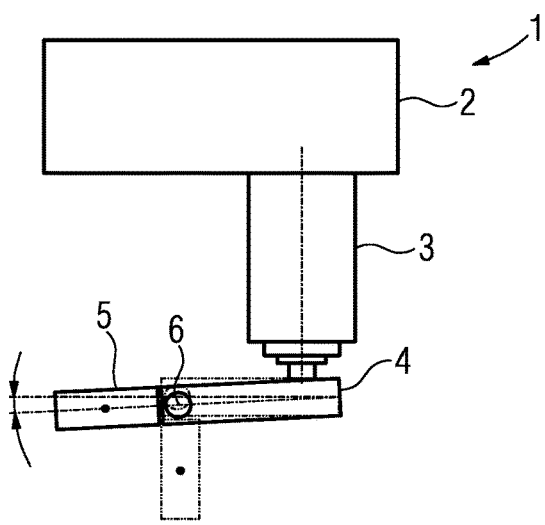
FIG. 2 shows one embodiment of a stand with deformation of a horizontal bracket.

FIG. 2 illustrates one embodiment of the stand 1 with the X-ray source or the X-ray detector 5, as explained above. The vertical arm 3, which is mounted on the top support 2, is set to a minimal length. An inclination of the vertical arm 3 relative to the vertical is therefore minimized.

The X-ray detector or X-ray detector 5 is shown in both a horizontal orientation and, rotated about the pivot 6, a vertical orientation (e.g., marked by a dashed line). The distance of the center of gravity of the X-ray source or X-ray detector 5 from the vertical axis of the vertical arm 3 is noticeably smaller in the case of vertical orientation of the X-ray source or X-ray detector 5. This reduces the leverage that is exerted by the force due to weight of the X-ray source or X-ray detector 5 via the horizontal bracket 4 on the vertical arm 3 or on the support of the horizontal bracket 4 in the vertical arm 3. A horizontally oriented X-ray source or X-ray detector 5 therefore produces greater deforming forces on the stand than a vertically oriented X-ray source or X-ray detector 5. The consequently greater deformation in the case of a horizontal X-ray source or X-ray detector 5 results in greater inclination thereof relative to the horizontal, as indicated by two angle arrows in the illustration.

FIG. 2 shows that a change in the horizontal length of the horizontal bracket 4 is produced as a result of rotating the X-ray source or X-ray detector 5 about the pivot 6. Though not shown in FIG. 2, the horizontal bracket 4 may also be length-adjustable in a horizontal direction via a telescopic tube assembly or similar mechanism.

Figure 3:
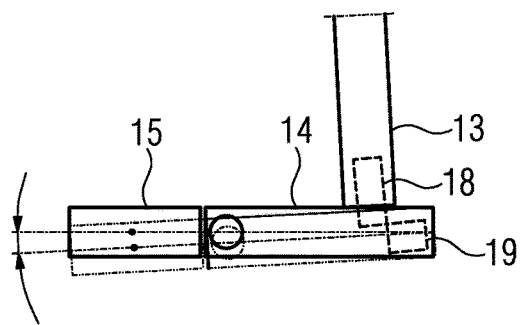
FIG. 3 shows one embodiment of a stand with an adjustment device.

FIG. 3 shows the vertical arm 13 of a stand in a position that is deformed (e.g., inclined relative to the vertical) by the force due to weight of the X-ray source or X-ray detector 15. A horizontal bracket 14 that holds the X-ray source or X-ray detector 15 is mounted on the vertical arm 13.

An inclination-angle sensor 19 is arranged in the bracket 14 and detects an inclination of the bracket 14 relative to the horizontal. The inclination of the bracket 14 relative to the horizontal is produced as a result of the deformation of the vertical arm 13 and of the mounting of the horizontal bracket 14 in the vertical arm 13. The inclination-angle sensor 19 therefore detects a measure that is essentially directly a measure of the deformation of the stand. The inclination signal of the inclination-angle sensor 19 is used to activate a motor 18. The motor 18 is activated as a function of the inclination signal, and hence as a function of the deformation that occurs in each case, such that the inclined horizontal bracket 14 (e.g., marked by a dashed line) is adjusted into an alignment that is as precisely as possible horizontal (e.g., unbroken lines). In this respect, the inclination-angle sensor 19 and the motor 18 are components of a device for compensating for the deformation of the stand.

Figure 4:
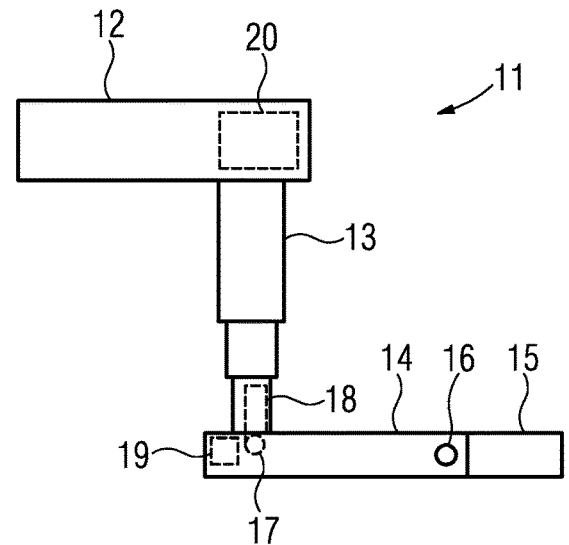
FIG. 4 shows one embodiment of a stand with an inclination-angle sensor and an adjustment device.

FIG. 4 shows one embodiment of the stand 11 of the vertical arm 13 explained above. The vertical arm 13 is mounted on a top support 12. The top support 12 includes a control device 20. The purpose of the control device 20 is to control the stand in order to compensate for deformation of the stand 11 as explained above.

A horizontal bracket 14 is mounted onto the vertical arm 13. The horizontal bracket 14 holds an X-ray source or X-ray detector 15 that is movably mounted thereon via a pivot 16.

The inclination-angle sensor 19, as explained above, is arranged in the horizontal bracket 14. The inclination-angle sensor 19 is connected (not shown in the illustration) to the control device 20 such that the control device 20 receives an inclination signal from the inclination-angle sensor 19. The control device 20 (likewise not shown) is also connected to the motor 18, which the control device 20 controls as a function of the inclination signal. The motor 18 drives an adjustment device 17, which is not shown in greater detail. The adjustment device 17 may be, for example, a setting screw, a tapered disc, an eccentric, a spindle drive or the like.

Therefore, the control device 20, the inclination-angle sensor 19, the motor 18 and the adjustment device 17 together form a device for compensating for a deformation of the stand 11. If the horizontal bracket 14 is inclined relative to the horizontal due to deformation of the stand 11, the control device 20 regulates the inclination of the bracket 14 based on the inclination signal from the inclination-angle sensor 19 by activating the motor 18 such that the bracket 14 is returned to the horizontal.

Depending on the degree of freedom of movement of the stand and an intended use of the stand, the desired position of the horizontal bracket 14 may also vary from the horizontal (e.g., from the level). In this case, the control device 20 regulates the compensating device such that the desired inclination angle of the horizontal bracket 14 relative to the level is maintained irrespective of any deformation of the stand 11.

Figure 5:
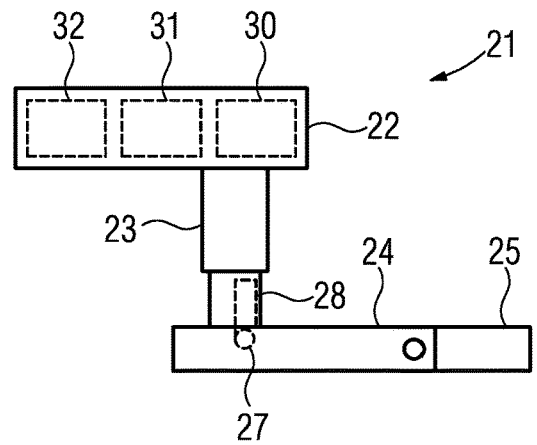
FIG. 5 shows one embodiment of a stand with an inclination-angle transmitter and an adjustment device.

FIG. 5 shows one embodiment of a stand 21 with a vertical arm 23 and a horizontal bracket 24. The vertical arm 23 is configured so as to be length-adjustable, as explained above. The horizontal bracket 24 holds an X-ray source or X-ray detector 25 that is movably mounted thereon, as explained above.

A motor 28 drives an adjustment device 27 that may adjust the horizontal inclination of the horizontal bracket 24. The adjustment compensates for deformations of the stand 21. The motor 28 is activated by a control device 30. The control device 30 is connected to an inclination-angle transmitter 31 and receives an inclination signal therefrom. The signal represents a measure of the inclination of the bracket 24 relative to the horizontal.

The inclination-angle transmitter 31 receives a vertical position signal and may also receive a horizontal position signal from the stand control device 32. The signal relates to the respective position of the bracket 24. The vertical position signal represents information about the vertical longitudinal position of the vertical arm 23. The horizontal position signal represents information about the orientation of the X-ray source or X-ray detector 25 relative to the horizontal bracket 24 (e.g., horizontally or vertically oriented X-ray source or X-ray detector 25). In the sense explained above, this represents information about the horizontal longitudinal position of the bracket 24. The bracket 24 may also be length-adjustable, such that a corresponding longitudinal position may also be supplied to the inclination-angle transmitter 31 by the stand control device 32.

The unwanted deformation of the stand 21 occurring in each case is determined by the inclination-angle transmitter 31 as a function of the respective vertical and horizontal position of the horizontal bracket 24, and of the X-ray source or X-ray detector 25, respectively. The information used for this purpose may be determined empirically beforehand and stored in the inclination-angle transmitter 31. In this case, the deformation occurring for each vertical and horizontal position of the stand 21 (e.g., the respective inclination angle of the horizontal bracket 24) is measured and stored in relation to the position data. The previously measured deformation data may be inferred from the position data during operation of the stand 21. In this way, the adjustment device 27 may be controlled without the need for an inclination-angle sensor.

Figure 6:
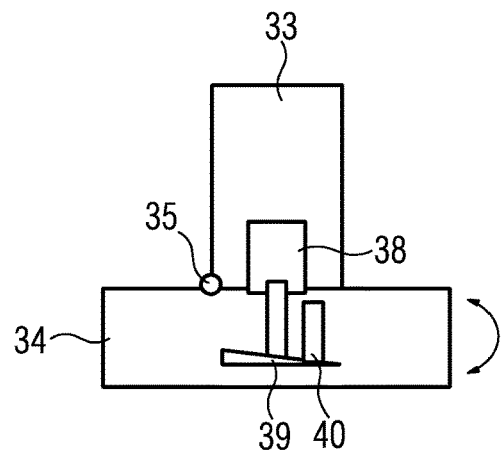
FIG. 6 shows one embodiment of a stand with an adjusting element in the form of a tapered disc.

FIG. 6 schematically shows one embodiment of a stand with a tapered-disc adjusting element. A tapered disc 39 that is driven by a motor 38 is used to adjust the inclination angle of the horizontal bracket 34. In this case, the inclination angle may be adjusted about a center of rotation 35 that may be embodied as a pivot. The motor 38 with tapered disc 39 is securely supported on a vertical telescopic tube assembly 33. The tapered disc 39 interacts with a plunger 40 that is securely supported on the horizontal bracket 34. In the position illustrated, the tapered disc 39 has a minimal thickness at a point of contact with the plunger 40. If the tapered disc 39 is rotated by the motor 38 such that the tapered disc 39 has a greater thickness at the point of contact, the plunger 40 is pushed upwards, and the inclination angle of the horizontal bracket 34 is consequently adjusted in a counterclockwise direction.

Figure 7:
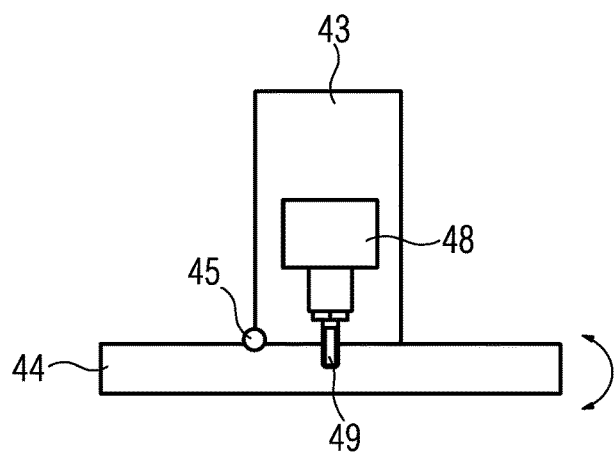
FIG. 7 shows one embodiment of a stand with an adjusting element in the form of an actuating screw thread.

FIG. 7 schematically shows one embodiment of a stand with a screw-thread adjusting element. A motor 48 with a screw-thread drive 49 is securely supported on the vertical telescopic tube assembly 43. The screw-thread drive 49 is driven by the motor 48 and interacts with a corresponding counterpart, which is securely supported in the horizontal bracket 44. In this case, a male thread may be arranged on the motor side, and a female thread may be arranged on the bracket side, for example. The inclination angle of the horizontal bracket 44 may be adjusted about a center of rotation 45 that may be embodied as a pivot. If the screw-thread drive 49 is driven by the motor 48 such that the motor-side part is driven further into the bracket-side counterpart, the bracket 44 is then pulled upwards, and the inclination angle of the horizontal bracket 44 is consequently adjusted in a counterclockwise direction.

Figure 8:
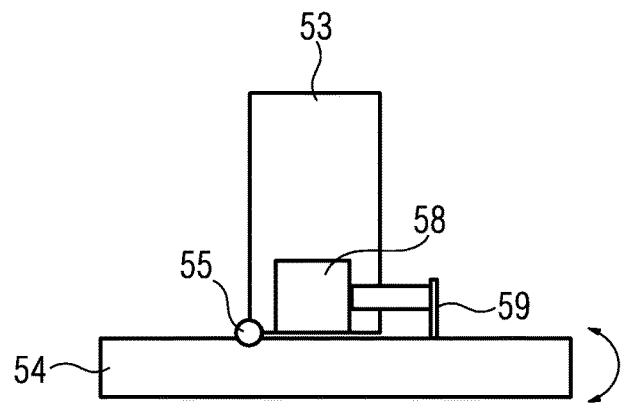
FIG. 8 shows one embodiment of a stand with an eccentric adjusting element.

FIG. 8 schematically shows one embodiment of a stand with eccentric adjustment. A motor 58 with an eccentric disc 59 is securely supported on the vertical telescopic tube assembly 53. The eccentric disc 59 is driven by the motor 58 and interacts with a corresponding counterpart, which is securely supported in the horizontal bracket 54. In this case, for example, a pin may be eccentrically arranged on the eccentric side, and a guiding groove, into which the pin engages and by which the pin is guided, may be arranged on the bracket side. The arrangement of pin and groove may also be reversed. Instead, an adjustment arm that is rotatably mounted on both sides may also be connected to the bracket 54 and eccentrically to the eccentric 59. The inclination angle of the horizontal bracket 54 may be adjusted about a center of rotation 55 that may be embodied as a pivot. If the eccentric 59 is driven by the motor 58 such that the eccentrically arranged effective point (e.g., pin, groove or adjustment arm mounting) is moved upwards, the bracket 54 is then pulled upwards, and the inclination angle of the horizontal bracket 54 is consequently adjusted in a counterclockwise direction.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A stand comprising:
an assembly;
a bracket, the bracket being a horizontal bracket, the horizontal bracket being rotatably connected to the assembly via a pivot; and
a device for distortion compensation comprising:
an inclination-angle transmitter configured to generate an inclination signal as a function of an inclination angle of the horizontal bracket;
a control device configured to receive the inclination signal from the inclination-angle transmitter;
a motor drive that is activated by the control device; and
an adjustment device comprising a tapered disc that is driven by the motor drive and is configured to adjust the inclination angle of the horizontal bracket about the pivot,
wherein the control device is configured to activate the motor drive such that any deviation of the inclination angle of the horizontal bracket from a predefined inclination angle is reduced.

2. The stand of claim 1, wherein the inclination-angle transmitter is an inclination-angle sensor.

3. The stand of claim 1, wherein the assembly is vertically length-adjustable and configured to support the horizontal bracket, and
wherein the inclination-angle transmitter is configured to:
receive a vertical position signal from the control device, the vertical position signal being correlated to a vertical length adjustment of the assembly; and
generate the inclination signal depending on the vertical position signal.

4. The stand of claim 3, wherein the horizontal bracket comprises a horizontally length-adjustable bracket,
wherein the inclination-angle transmitter is configured to:
receive a horizontal position signal from the control device, the horizontal position signal being correlated to a horizontal length position of the horizontal bracket; and
generate the inclination signal depending on the horizontal position signal.

5. The stand of claim 4, wherein an X-ray detector or an X-ray source is supported on the horizontally length-adjustable bracket.

6. The stand of claim 1, further comprising:
a plunger fixably attached to the horizontal bracket,
wherein the motor drive is fixably mounted to the assembly,
wherein the plunger and the tapered disc interact at a point of contact, and
wherein the tapered disc is configured to raise or lower the plunger, and thereby raise or lower the horizontal bracket, as the tapered disc is rotated by the motor drive, depending on a thickness of the tapered disc at the point of contact.

7. A stand comprising:
an assembly;
a bracket, the bracket being a horizontal bracket, the horizontal bracket being rotatably connected to the assembly via a pivot; and
a device for distortion compensation comprising:
an inclination-angle transmitter configured to generate an inclination signal as a function of an inclination angle of the horizontal bracket;
a control device configured to receive the inclination signal from the inclination-angle transmitter;
a motor drive that is supported by the assembly and activated by the control device; and
an adjustment device that is supported by the horizontal bracket, driven by the motor drive, and configured to adjust the inclination angle of the horizontal bracket about the pivot,
wherein the control device is configured to activate the motor drive such that any deviation of the inclination angle of the horizontal bracket from a predefined inclination angle is reduced, and
wherein the adjustment device comprises a tapered disc in contact with a plunger at a contact point.

8. The stand of claim 7, wherein the adjustment device comprises a screw thread drive.

9. The stand of claim 7, wherein the adjustment device comprises an eccentric disc.

10. The stand of claim 7, wherein the inclination-angle transmitter is an inclination-angle sensor.

11. A stand comprising,
an assembly;
a bracket, the bracket being a horizontal bracket, the horizontal bracket being rotatably connected to the assembly via a pivot; and
a device for distortion compensation comprising:
   an inclination-angle transmitter configured to generate an inclination signal as a function of an inclination angle of the horizontal bracket;
   a control device configured to receive the inclination signal from the inclination-angle transmitter;
   a motor drive that is supported by the assembly and activated by the control device; and
   an adjustment device that is supported by the horizontal bracket, driven by the motor drive, and configured to adjust the inclination angle of the horizontal bracket about the pivot,
wherein the control device is configured to activate the motor drive such that any deviation of the inclination angle of the horizontal bracket from a predefined inclination angle is reduced,
wherein the assembly is vertically length-adjustable and configured to support the horizontal bracket, and
wherein the inclination-angle transmitter is configured to:
   receive a vertical position signal from the control device, the vertical position signal being correlated to a vertical length adjustment of the assembly; and
   generate the inclination signal depending on the vertical position signal.

12. The stand of claim 11, wherein the horizontal bracket comprises a horizontally length-adjustable bracket,
wherein the inclination-angle transmitter is configured to:
   receive a horizontal position signal from the control device, the horizontal position signal being correlated to a horizontal length position of the horizontal bracket; and
   generate the inclination signal depending on the horizontal position signal.

13. The stand of claim 12, wherein an X-ray detector or an X-ray source is supported on the horizontally length-adjustable bracket.

14. The stand of claim 7,
wherein the plunger is supported by the horizontal bracket, and
wherein the tapered disc is configured to raise or lower the plunger, and thereby raise or lower the horizontal bracket, as the tapered disc is rotated by the motor drive, depending on the thickness of the tapered disc at the point of contact.

15. The stand of claim 11, wherein the inclination-angle transmitter is an inclination-angle sensor.

* * * * *